(12) United States Patent
Hancock et al.

(10) Patent No.: US 6,282,964 B1
(45) Date of Patent: Sep. 4, 2001

(54) ELECTROMAGNETIC ACOUSTIC TRANSDUCER (EMAT) INSPECTION OF CRACKS IN BOILER TUBES

(75) Inventors: Jimmy W. Hancock; Daniel T. MacLauchlan, both of Lynchburg, VA (US); Ralph D. Murphy, Uniontown, OH (US)

(73) Assignees: The Babcock & Wilcox Co; McDermott Technology, Inc.

( * ) Notice: Subject to any disclaimer, the term of this patent is extended or adjusted under 35 U.S.C. 154(b) by 0 days.

(21) Appl. No.: 09/398,621

(22) Filed: Sep. 17, 1999

(51) Int. Cl.⁷ .................................................. G01N 29/00
(52) U.S. Cl. ................................................................ 73/622
(58) Field of Search ............................ 73/618, 620, 622, 73/627, 632, 633, 635, 637, 638, 640, 643

(56) References Cited

U.S. PATENT DOCUMENTS

| | | | |
|---|---|---|---|
| 5,035,143 | * 7/1991 | Latimer et al. | 73/598 |
| 5,085,082 | * 2/1992 | Cantor et al. | 73/622 |
| 5,359,898 | * 11/1994 | Latimer | 73/600 |
| 5,456,113 | * 10/1995 | Kwun et al. | 73/587 |
| 5,526,691 | * 6/1996 | Latimer et al. | 73/592 |
| 5,763,786 | * 6/1998 | Camplin et al. | 73/643 |
| 5,907,100 | * 5/1999 | Cook | 73/602 |
| 6,009,756 | * 1/2000 | Willems et al. | 73/643 |
| 6,070,467 | * 6/2000 | Rosenberg et al. | 73/643 |

* cited by examiner

Primary Examiner—Richard A. Moller
(74) Attorney, Agent, or Firm—Robert J. Edwards; Eric Marich

(57) ABSTRACT

An EMAT device for non-destructive inspection of the surface of a tube for cracks using acoustic surface waves includes a pulsed magnet having an active surface for facing the surface of a tube to be inspected. A receive emat coil is on the active surface and a transmit emat coil is on the opposite surface of the receive coil. The transmit emat coil has a scan surface for scanning over the tube surface. A transmitter for generating and transmitting an RF signal to the transmit emat coil is provided for generating a transmitted acoustic wave signal along the tube, the transmitted wave creating a reflected acoustic wave if a crack in the tube is encountered, the reflected wave generating a reflection signal in the receive emat coil. A receiver is connected to the receive emat coil for receiving the reflection signal. A digital computer is connected to the receiver for receiving and for processing the reflection signal and a display displays information about a crack in the tube which created the reflected acoustic wave and resulting reflection signal.

9 Claims, 4 Drawing Sheets

EMAT SURFACE WAVE INSPECTION FOR CRACKS ON OD OF BOILER TUBES

Scan of Calibration Standard Showing Signals From 0.009" & 0.040" Deep Edm Notches and Natural Crack

ELECTROMAGNETIC ACOUSTIC TRANSDUCER (EMAT) INSPECTION OF CRACKS IN BOILER TUBES

FIELD AND BACKGROUND OF THE INVENTION

The present invention relates generally to the field of non-destructive testing of components and in particular to a new and useful method and apparatus for the non-destructive inspection of boiler tubes for cracks using electromagnetic acoustic transducer technology.

Various nondestructive methods such as ultrasonic (UT), eddy current (ET), magnetic particle (MT), and dye penetrant (PT), have been used for the detection of cracks in boiler tubes. All have serious limitations that prevent their use for real time, high speed inspection of boilers for surface breaking cracks. UT requires a liquid couplant which can produce extraneous signals. EC is very susceptible to material properties/variations inherent within a material which can produce signals that mask the defect signals or can be mistakenly interpreted as defects. Both MT and PT require large amounts of chemicals and are not suited for high speed inspection of boilers due to the time required for chemical application and signal interpretation, plus disposal of used chemicals.

Electromagnetic acoustic transducers (here EMATs or emats) are known for use in testing materials for defects. In known systems, a signal generator creates an acoustic wave which propagates through a test material and either the original signal or a reflection is received by a single sensor having a coil for converting acoustic wave energy to an electrical current. EMATs are typically used on planar surfaces of a test material to detect both surface and subsurface defects in the test material.

Tubes present a challenge for testing due to their curved surfaces. Tubes used in industrial boilers present a further challenge, as the space around and access to the tubes is typically very limited. These tubes must be as free of defects as possible, and coated with materials to resist corrosion and breakdown in the harsh environment of an industrial boiler.

SUMMARY OF THE INVENTION

It is an object of the present invention to provide an EMAT device for non-destructive inspection of the surface of a tube for cracks using acoustic surface waves which includes a pulsed magnet having an active surface for facing the surface of a tube to be inspected. A receive emat coil is on the active surface and a transmit emat coil is on the opposite surface of the receive coil. The transmit emat coil has a scan surface for scanning over the tube surface. A transmitter for generating and transmitting an RF signal to the transmit emat coil is provided for generating a transmitted acoustic wave signal around the tube, the transmitted wave creating a reflected acoustic wave if a crack in the tube is encountered, the reflected wave generating a reflection signal in the receive emat coil. A receiver is connected to the receive emat coil for receiving the reflection signal. A digital computer is connected to the receiver for receiving and for processing the reflection signal and a display displays position information about a crack in the tube which created the reflected acoustic wave and resulting reflection signal.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
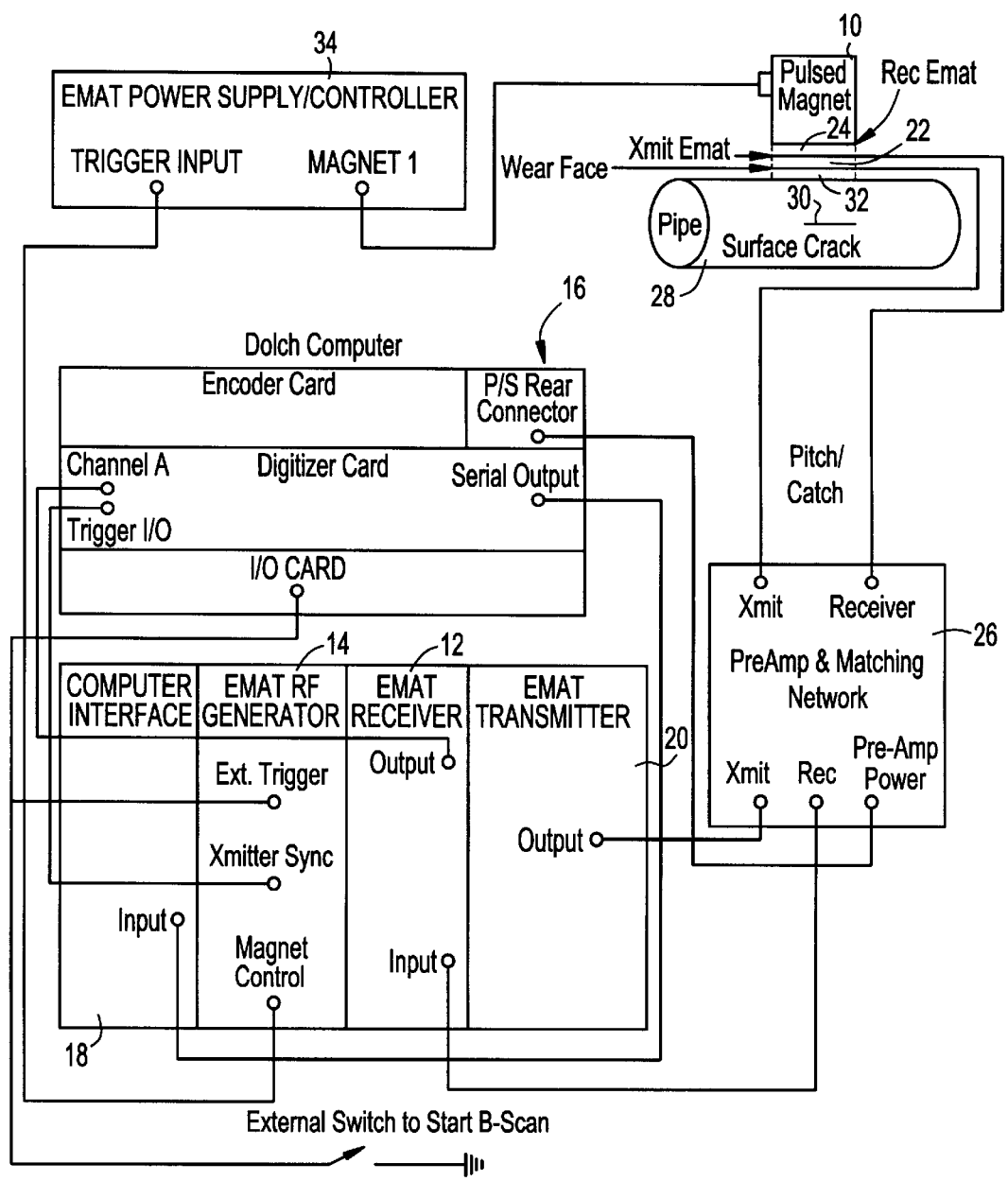
FIG. 1 is a schematic diagram of a testing device according to the invention.

Referring now to the drawings, in which like reference numerals are used to refer to the same or similar elements, FIG. 1 is a schematic diagram showing the components of an electromagnetic acoustic transducer testing device of the invention.

Figure 2:
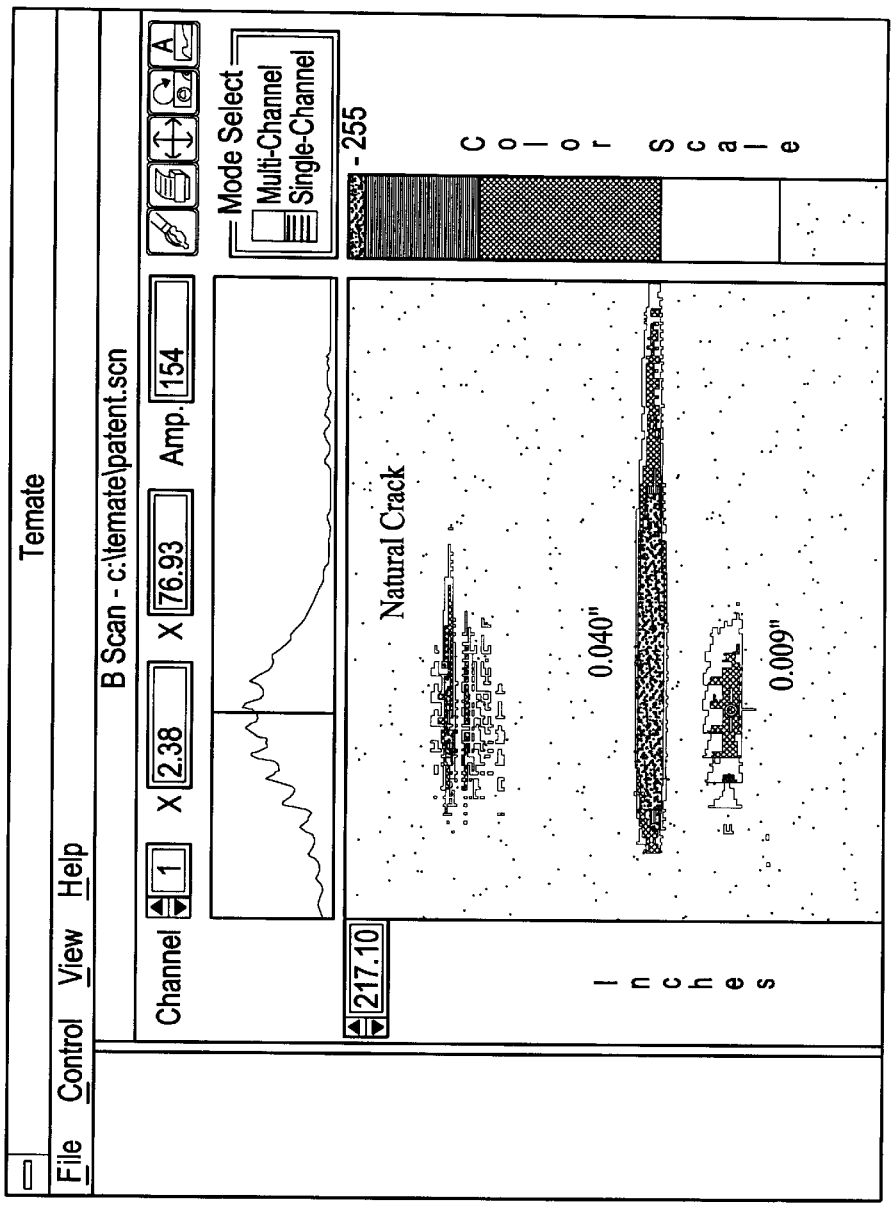
FIG. 2 is an illustration of a computer output display of the invention.

The test system shown in FIG. 1 comprises custom EMAT electronics, including an emat pulser or transmitter 20, receiver 12, RF generator 14, and computer interface 18. RF pulsed magnet on a probe head 10, transmit and receiver emats 22, 24, preamp and matching networks 26, and cables are also included. The unique pulsed magnet and surface wave emat assembly are mounted in a hand held housing that is rolled down the tubes at approximately 6-inches/second while acquiring the data in real time. The magnet is powered by power supply 34. A surface wave is generated in the tube 28 by the magnetic field from the pulsed magnet or head 10 and eddy currents produced by the transmit emat coil 22. This surface wave is bi-directional and follows the tube surface circumferentially until it is reflected back by a longitudinal crack 30 originating from the tube OD surface. This reflected signal returns to the emat receiver coil 24, where it is detected, amplified, digitized, and displayed on a computer screen (FIG. 2) in both A-scan and B-scan format for easy operator evaluation. The data can then be saved to disc if desired.

In FIG. 1, a digital decoder with encoding card and I/O card for the computer 18 is shown at 16.

The technique and system of the invention uses a specially modified pulsed magnet, surface waves, and B-scan display to allow high rates of scanning and on-line evaluation. The design of the pulsed magnet and drive pulse have been optimized to make both as small as possible. In particular, the width of one pole piece of the magnet was minimized to allow the probe to be operated as close as possible to the adjacent boiler tube. This is extremely important in emat operations because of the large amplitude "main bang" signal produced by the emat pulser/transmit emat. If the distance from the emats to the area of inspection is not sufficient, no return signal from the crack will be detected as it will be lost in the main bang.

In conjunction with the modified pulsed magnet, focused surface wave emat coil assemblies with conformal backing in the form of a wear face 32 was used to provide minimum lift-off to the tube surface. This allowed a small, lightweight probe to be fabricated that could be easily scanned at high speeds. This test provides a fast (a complete boiler was inspected at a Louisiana utility with a two-man crew in 32 hours) and sensitive (calibrate on a 0.009" deep EDM notch, detection threshold ~0.005") real-time inspection of boiler water-wall tubes for surface breaking cracks.

Utilities have previously used dye penetrant or wet magnetic particle inspection to test for surface cracks on the OD's of boiler tubes. These methods are both time consuming and require large amounts of chemicals when inspecting a complete boiler. Also the sensitivity of these tests did not meet the requirements of the utility where we performed the emat surface wave inspections, as they were still experiencing forced outages between scheduled shutdowns because of tube failures due to cracking of the boilers water-wall tubes. This utility has reported no failures or unscheduled outages due to water-wall tube failures since their units were inspected with this technique.

The pulsed magnet may have one or both poles modified in order to escape the "main bang" signals, the pulsed magnet and surface wave emats may be modified to detect longitudinal, circumferential or off-axis cracking, this cracking may be detected on the "hot" or "cold" (casing) side of the boiler tubes. Other test frequencies may be employed, and the data can be displayed in numerous ways, however the B-Scan method with the signal amplitude displayed in color ranges is an excellent method of presenting the data to the operator for real-time evaluation.

Wear face or backing 32 is made of ultra high molecular weight (UHMW) plastic or other wear resistant material which allows the coil head to slide along the outer surface of the tube but not interfere with the emat signals from transmit (Xmit) emat coil 22 or to receive (Rec) emat coil 24. Coils 22 and 24, as well as face 32 are flexible and contour to the tube diameter, and the lower active surface or face of pulse magnet 10 can be curved or contoured to closely engage the tube surface.

Figure 3:
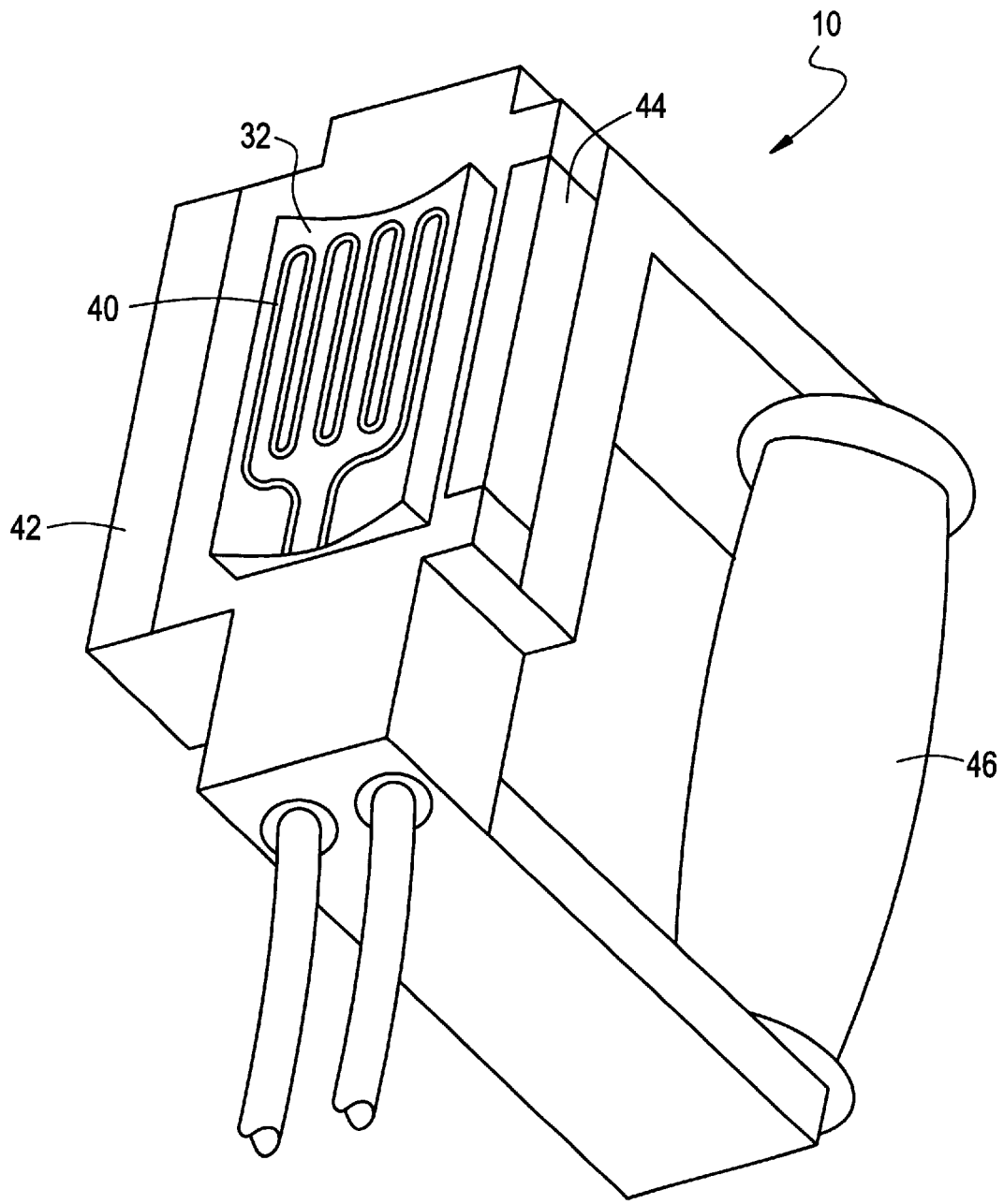
FIG. 3 is a schematic perspective view of a probe of the invention.

FIG. 3 illustrated the probe head 10 which is shown with the active wear surface of UHMW plastic 32 toward the viewer. Legs 40 of the emat coil, which is a pitch-catch coil, are visible beneath the wear surface. Magnetic poles 42 and 44 are also visible, with pole 44 being narrower than pole 42, for increased tube surface coverage. A handle 46 is connected to the frame of probe head 10 so that the probe head can be manually scanned along the tube surface to be tested.

Figure 4:
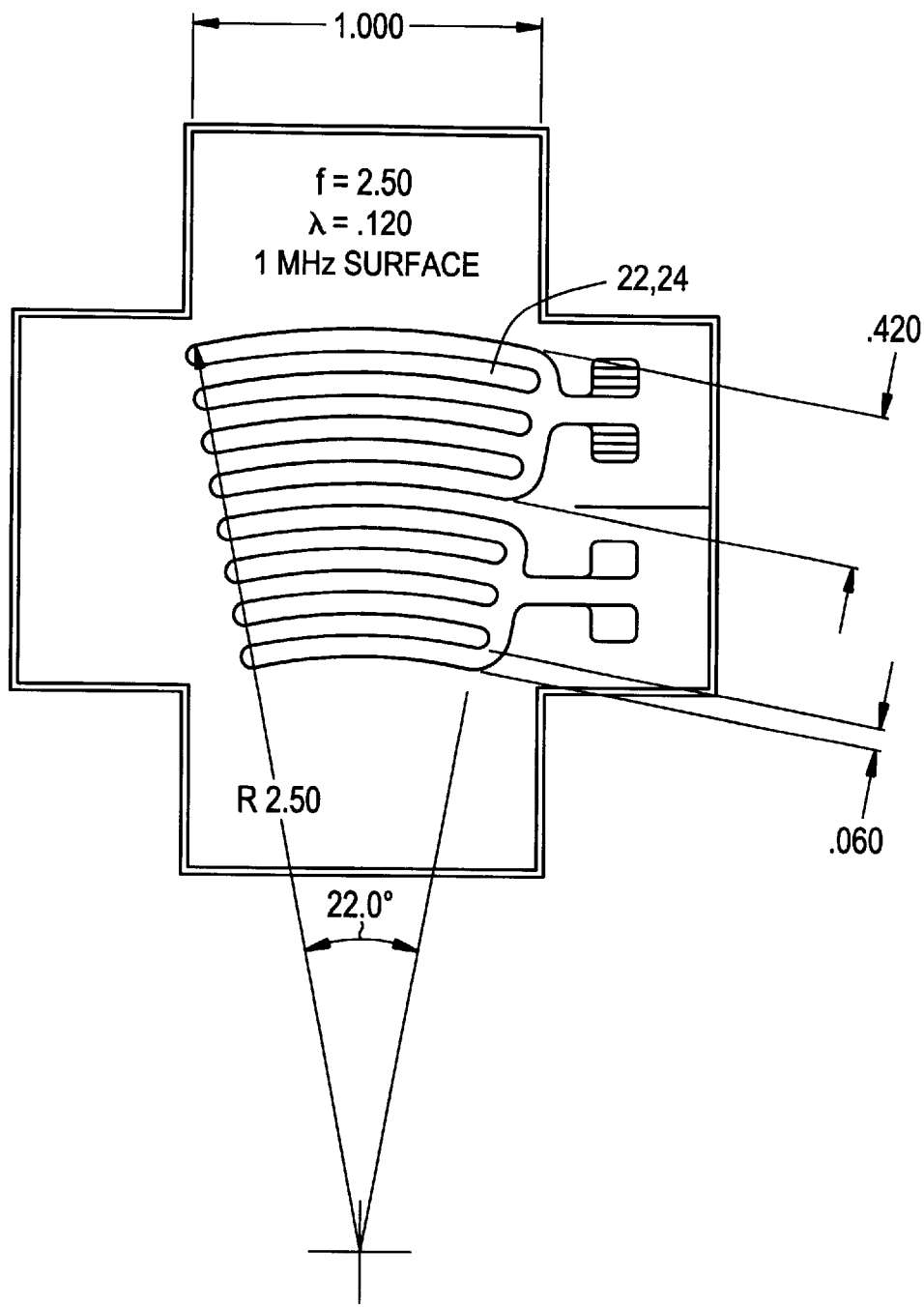
FIG. 4 is a schematic illustration of a typical emat coil pattern and dimensions used by the present invention.

FIG. 4 illustrates typical dimensions and coil patterns for the emat coils 22, 24.

While a specific embodiment of the invention has been shown and described in detail to illustrate the application of the principles of the invention, it will be understood that the invention may be embodied otherwise without departing from such principles.

What is claimed is:

1. An EMAT device for real-time non-destructive inspection of the surface of a tube for cracks using acoustic surface waves, the device comprising:

a pulsed magnet having an active surface for facing the surface of a tube being inspected;

a receive EMAT coil on the active surface, the receive EMAT coil having a second surface opposite the active surface;

a transmit EMAT coil on the second surface of the receive EMAT coil, the transmit EMAT coil having a scan surface opposite the second surface, the scan surface for scanning over the tube surface;

a transmitter for generating and transmitting an RF signal to the transmit EMAT coil for generating a transmitted acoustic wave signal along the tube, the transmitted wave creating a reflected acoustic wave if a crack in the tube is encountered, the reflected wave generating a reflection signal in the receive EMAT coil;

a receiver connected to the receive EMAT coil for receiving the reflection signal;

digital computing means connected to the receiver for receiving and for processing the reflected signal; and display means for displaying real-time information about a crack in the tube which has created the reflected acoustic wave and resulting reflected wave.

2. An EMAT device according to claim 1, wherein the coils are flexible and contour to closely engage the surface of the tube.

3. An EMAT device according to claim 1, wherein the coils and the active surface are contoured to closely engage the surface of the tube.

4. An EMAT device according to claim 1, including a wear face over the scan surface of the transmit emat coil.

5. An EMAT device according to claim 4, wherein the wear face and the coils are flexible.

6. An EMAT device according to claim 4, wherein the wear face is made of UHMW plastic.

7. An EMAT device according to claim 1, wherein the digital computing means including means for displaying, on the display means, information about the presence, the size and the position of a crack on the tube.

8. An EMAT device for non-destructive inspection of the surface of a tube for cracks using acoustic surface waves, the device comprising:

a pulsed magnet having an active surface for facing the surface of a tube being inspected;

a receive EMAT coil on the active surface, the receive EMAT coil having a second surface opposite the active surface;

a transmit EMAT coil on the second surface of the receive EMAT coil, the transmit EMAT coil having a scan surface opposite the second surface, the scan surface for scanning over the tube surface, the pulsed magnet and the EMAT coils being mounted on a common probe head having a handle connected to the probe head for holding and scanning the active surface along the surface of the tube;

a transmitter for generating and transmitting an RF signal to the transmit EMAT coil for generating a transmitted acoustic wave signal along the tube, the transmitted wave creating a reflected acoustic wave if a crack in the tube is encountered, the reflected wave generating a reflection signal in the receive EMAT coil;

a receiver connected to the receive EMAT coil for receiving the reflection signal;

digital computing means connected to the receiver for receiving and for processing the reflected signal; and display means for displaying real-time information about the presence, size and position of a crack in the tube which has created the reflected acoustic wave and resulting reflected wave.

9. An EMAT device according to claim 1, wherein the pulsed magnet has a pair of poles on opposite sides of the active surface, one pole being narrower than the other.

* * * * *